United States Patent
Yang et al.

(10) Patent No.: US 9,878,069 B2
(45) Date of Patent: Jan. 30, 2018

(54) MINERALIZED COLLAGEN-BASED FEMORAL HEAD SUPPORT DEVICE

(71) Applicant: Shuhua Yang, Wuhan, Hubei (CN)

(72) Inventors: Shuhua Yang, Hubei (CN); Changming Wang, Beijing (CN); Zhiye Qiu, Beijing (CN); Fuzhai Cui, Beijing (CN); Xianzhe Liu, Hubei (CN); Weihua Xu, Hubei (CN); Shunan Ye, Hubei (CN); Jing Wang, Hubei (CN); Yiping Zhang, Zhejiang (CN); Yali Li, Zhejiang (CN)

(73) Assignee: Shuhua Yang, Wuhan (CN)

( * ) Notice: Subject to any disclaimer, the term of this patent is extended or adjusted under 35 U.S.C. 154(b) by 0 days.

(21) Appl. No.: 15/024,088

(22) PCT Filed: Mar. 21, 2014

(86) PCT No.: PCT/CN2014/073874
§ 371 (c)(1),
(2) Date: Mar. 23, 2016

(87) PCT Pub. No.: WO2015/039418
PCT Pub. Date: Mar. 26, 2015

(65) Prior Publication Data
US 2016/0235891 A1 Aug. 18, 2016

(30) Foreign Application Priority Data

Sep. 23, 2013 (CN) .......................... 2013 1 0433477

(51) Int. Cl.
*A61L 27/46* (2006.01)
*B29C 43/00* (2006.01)
(Continued)

(52) U.S. Cl.
CPC .............. *A61L 27/46* (2013.01); *A61B 17/58* (2013.01); *A61B 17/68* (2013.01); *A61B 17/72* (2013.01);
(Continued)

(58) Field of Classification Search
CPC ......... A61L 27/46; A61L 27/50; A61B 17/58; A61B 17/68; A61B 17/72; A61B 17/74;
(Continued)

(56) References Cited

U.S. PATENT DOCUMENTS 5,084,050 A * 1/1992 Draenert ............ A61F 2/30767
606/304
5,455,231 A 10/1995 Constantz et al.
(Continued)

FOREIGN PATENT DOCUMENTS

| CN | 1338315 A | 3/2002 |
|---|---|---|
| CN | 102028566 A | 4/2011 |
| WO | 2006047310 A2 | 5/2006 |

OTHER PUBLICATIONS

International Search Report of PCT Patent Application No. PCT/CN2014/073874 dated Jun. 11, 2014.
(Continued)

*Primary Examiner* — Walter B Aughenbaugh

(57) ABSTRACT

A femoral head support device, in particular a mineralized collagen-based femoral head support device applicable to the treatment of early osteonecrosis of femoral head. The device is made from a dense, homogeneous organic/inorganic composite, wherein the organic phase includes collagen and inorganic phase includes nano calcium phosphate salt, and the device is of a cylinder having an upright through hole and also has a support strength of up to 4000-6000N. By implementing a method for manufacturing such mineralized collagen-based femoral head support device, the (Continued)

mineralized collagen-based femoral head support device with mechanical properties equivalent to human cortical bone can be manufactured; and the mineralized collagen-based femoral head support device can meet the demand for clinical treatment of early osteonecrosis of femoral head to avoid the continuous collapse of necrotic femoral head.

6 Claims, 4 Drawing Sheets

(51) Int. Cl.
*A61B 17/68* (2006.01)
*A61B 17/58* (2006.01)
*A61B 17/72* (2006.01)
*B29C 43/02* (2006.01)
*A61L 27/42* (2006.01)
*A61F 2/28* (2006.01)
*A61F 2/32* (2006.01)
*A61L 27/50* (2006.01)
*A61B 17/74* (2006.01)
*B29L 31/00* (2006.01)

(52) U.S. Cl.
CPC ............. *A61F 2/2846* (2013.01); *A61F 2/32* (2013.01); *A61L 27/425* (2013.01); *A61L 27/50* (2013.01); *B29C 43/00* (2013.01); *B29C 43/006* (2013.01); *B29C 43/02* (2013.01); *B29C 43/027* (2013.01); *A61B 17/74* (2013.01); *A61L 2430/02* (2013.01); *A61L 2430/24* (2013.01); *B29C 43/003* (2013.01); *B29L 2031/7532* (2013.01); *Y10T 428/1372* (2015.01)

(58) Field of Classification Search
CPC ....... B29C 43/00; B29C 43/006; B29C 43/02; B29C 43/027; B29C 43/04; B29C 43/14; B29C 43/36; Y10T 428/1352; Y10T 428/1372; Y10T 428/139; Y10T 428/1393
See application file for complete search history.

(56) References Cited

U.S. PATENT DOCUMENTS

2010/0312355 A1* 12/2010 Yahav ................ A61L 27/025
623/23.61
2013/0345825 A1* 12/2013 Bufler ................ A61L 27/425
623/23.51
2014/0194363 A1* 7/2014 Hu ........................ A61K 38/39
514/16.7

OTHER PUBLICATIONS

1st Office Action of counterpart Chinese Patent Application No. 201310433477.4 dated Mar. 4, 2016.

* cited by examiner

MINERALIZED COLLAGEN-BASED FEMORAL HEAD SUPPORT DEVICE

TECHNICAL FIELD

The present application belongs to the technical field of biomedical materials, relates to a femoral head support device, and more particularly relates to a mineralized collagen-based femoral head support device which is applicable to the treatment of early osteonecrosis of femoral head.

BACKGROUND

Osteonecrosis of femoral head is a common orthopaedics disease, and a plurality of therapies for preventing the femoral head from collapsing are available at present. In these therapies, generally a hole is drilled, and a support is implanted, thereby jacking up the collapsed femoral head inside-out. The supports commonly used in clinic include: metal support devices (such as, memory titanium alloy nets, tantalum rods, or the like), autogenous cortical bones (such as, autologous ilium), and allogeneic bone support device.

For a memory titanium-nickel alloy net, it is hard to control during the supporting process, which easily results in an insufficient support or an excessive support. For a metal support device (such as a tantalum rod), however, after it is implanted into the femoral head, the femoral head is easily worn through and a new injure may be formed at last, since the modulus of elasticity of the metal support device is too high and does not match with the autogenous bone of a person. When the femoral head is collapsed further (such as entering later stage of phase III, phase IV, or phase V) and a hip replacement surgery needs to be carried out, the necrotic femoral head needs to be amputated; however, the metal support implanted in the femoral head is hard to be cut off, thereby the surgery time is extended, and the surgery becomes more difficult. The metal femoral head support device is the most widely-used support device in clinic. However, except for the mismatch of mechanical property between the metal femoral head support device and the autogenous bone, there is also a world of difference between compositions of the metal femoral head support device and those of the autogenous bone. Therefore, the metal materials used in the femoral head support device do not possess good biocompatibility, and can not be even degraded, and thus the autogenous bone can not be guided to grow.

In some case, taking out the autogenous cortical bone and further filling it in the necrotic areas of the femoral head can give a certain support to the femoral head. However, the strength of the implanted cortical bone is relative low, and the treatment efficacy is not ideal. Furthermore, a patient has only a limit number of autogenous bones, and taking out the autogenous bone during the surgery may bring a new wound to the patient, and thus the patient have to suffer more pain and medical expense burden.

It is possible to use allogeneic bones to prepare the support device for treating the collapse of the femoral head. However, few allogeneic bones meet the demands. During the practical producing process, due to the limitation of the skeletal size of a person, a femoral head support device which is made from an allogeneic bone and which has a length larger than 5 cm can not be prepared, and thus the clinical application thereof is greatly limited. Furthermore, several problems, such as having a limited source, immunogenicity, medical ethics problems, or the like, still exist in the allogeneic bones.

In conclusion, the therapies aiming at the collapse of the femoral head in the prior art respectively have defects, which results in a non-ideal treatment efficacy, and the early osteonecrosis of femoral head is further aggravated and finally collapsed, or the existing collapse is further aggravated, and thus the hip replacement surgery has to be carried out at least.

BRIEF SUMMARY

The object of the present application is to provide a collagen-based femoral head support device, aiming at the defects in the art. The material for preparing the support device is made from chemical compositions or structure prepared by the self-assembly of nano calcium phosphate salt and collagen molecule, and thus it has a biomimetic mineralization structure similar to the natural bone tissue of the human body. The chemical compositions in the support device are the same as those in the natural bone tissue, and thus the material has a good biocompatibility and osteogenic activity, and can be degraded, such that new bones can be guided to grow. In terms of mechanical property, the material has a mechanical strength similar to that of the cortical bone of the human body, and can provide sufficient mechanical support to the collapse portion of the femoral head. Meanwhile, the material has a modulus of elasticity similar to that of the cortical bone of the human body, and can not bring a new wound to the autogenous bone tissue of the patient. The present application further provides a preparation method for this kind of collagen-based femoral head support device.

In accordance with a first aspect of the present application, a mineralized collagen-based femoral head support device is provided. Wherein, the support device is made from a dense and homogeneous organic/inorganic composite. In this case, the organic phase includes collagen; while the inorganic phase includes nano calcium phosphate salt. A mass ratio of the organic phase to the inorganic phase of the composite is 9/1~4/6.

In one embodiment, a diameter of the nano calcium phosphate salt is 20~200 nm; a molar ratio of the calcium to the phosphate is 1/1~2/1.

In one embodiment, the mineralized collagen-based femoral head support device is a cylinder having an upright through-hole, and has an outer diameter of 9.0~11.0 mm, a through-hole diameter of 4.0~5.0 mm, and a length of 30.0~38.0 mm.

In one embodiment, an outer surface of the mineralized collagen-based femoral head support device has a roughness Ra of 3.2~25.0 μm.

In one embodiment, a thread is formed on an outer surface of the mineralized collagen-based femoral head support device; wherein the thread has a width of 0.25~1.0 mm, a depth of 0.2~0.8 mm, and a thread width of 1.5~2.5 mm.

In one embodiment, the mineralized collagen-based femoral head support device has a compressive strength of 4000~6000N in an axial direction thereof at most.

In accordance with a second aspect of the present application, a preparation method for the mineralized collagen-based femoral head support device according to the first aspect is further provided, which comprises the following steps:

Step S1, preparing mineralized collagen powder; wherein the preparation processes include:

Step S1-1, dissolving collagen into hydrochloric acid, nitric acid or acetic acid solution, thereby preparing acid solution having collagen, wherein a concentration of the collagen is $5.0 \times 10^{-5} \sim 5.0 \times 10^{-3}$ g/mL;

Step S1-2, continuously stirring the solution prepared by Step S1-1, and slowly and dropwise adding the solution containing calcium ions; wherein the addition amount of the calcium ions is 0.01~0.16 mol per gram of collagen;

Step S1-3, continuously stirring the solution prepared by Step S1-2, and slowly and dropwise adding the solution containing phosphate anions; wherein a molar ratio of the addition amount of the phosphate anions to the addition amount of the calcium ions in Step S1-2 is Ca/P=1/1~2/1;

Step S1-4, continuously stirring the solution prepared by Step S1-3, and slowly and dropwise adding NaOH solution until the mixed system has a pH of 6~8; wherein, when pH=5~6, the mixed system begins to precipitate; when pH=7, White suspension liquid appears in the mixed system;

Step S1-5, after 24~120 hours standing, separating precipitates in the mixed system prepared by Step S1-4, and washing away impurity ions; freeze-drying and grinding the precipitates, thereby obtaining the mineralized collagen powder for reserve;

Step S2, compression moulding a mineralized collagen bar; wherein the moulding processes include:

Step S2-1, weighting a certain amount of the mineralized collagen powder obtained by Step S1-5, and putting the powder into a cylindrical mould having a diameter of 9.0~11.0 mm;

Step S2-2, applying a pressure to the mould, and the pressure applied to the mineralized collagen powder is 900~1200 MPa, and then relieving the pressure; taking out an initial bar formed in the mould, turning the initial bar upside down, and further putting the initial bar into the mould again; applying a pressure to the mould again, and the pressure applied to the mineralized collagen initial rod is 900~1200 MPa;

Step S2-3, maintaining the pressure for 30~300 seconds, demoulding and thereby obtaining the mineralized collagen bar;

Step S3, machining the mineralized collagen bar; wherein the machining processes include:

Step S3-1, clamping the mineralized collagen bar obtained by Step S2-3 in a three jaw chuck of a lathe, drilling the bar from one end of the bar along a central axis thereof by means of a drill having a diameter of 4.0~5.0 mm; after the drill is drilled into the bar for half of the length of the bar, taking down the bar, and reversely clamping the bar at the three jaw chuck; drilling the bar from the other end of the bar until a through-hole is formed;

Step S3-2, taking down the mineralized collagen bar having a through-hole formed by Step S3-1; sleeving the bar on a frock having a diameter of 4.0~5.0 mm; clamping the bar in the three jaw chuck of the lathe, and cutting an outer edge of the bar, until the bar has a required outer diameter;

Step S3-3, turning a thread on an outer surface of the mineralized collagen bar; wherein the thread has a width of 0.25~1.0 mm, a depth of 0.2~0.8 mm, and a thread pitch of 1.5~2.5 mm;

Step S3-4, taking down the mineralized collagen bar, chamfering two ends of the bar at an angle of 45 degrees, thereby obtaining the mineralized collagen-based femoral head support device according to a first aspect of the present application.

When implementing the present application, the mineralized collagen-based femoral head support device having mechanical properties equivalent to the cortical bone of the human body can be prepared, and can meet the demands for the clinical treatment of early osteonecrosis of femoral head to prevent the continuous collapse of necrotic femoral head. The device is made from main compositions of the natural bone tissue of the human body including the collagen and the nano calcium phosphate salt or the like, and the nano calcium phosphate salt and the collagen are self-assembled to form a microstructure similar to the natural bone tissue, which provides an excellent microenvironment for the adhesion and the proliferation of the bone tissue. Therefore, the mineralized collagen-based femoral head support device according to the present invention has a good biocompatibility and excellent mechanical properties. In this way, a plurality of defects in the therapies for the femoral head in clinic can be avoided, and thus the support device of the present application has a broad prospect of application.

DETAILED DESCRIPTION OF THE PREFERRED EMBODIMENT

To better explain the disclosure in the present application, the present application will be further described with reference to the accompanying drawings and embodiments in the following.

Figure 1:
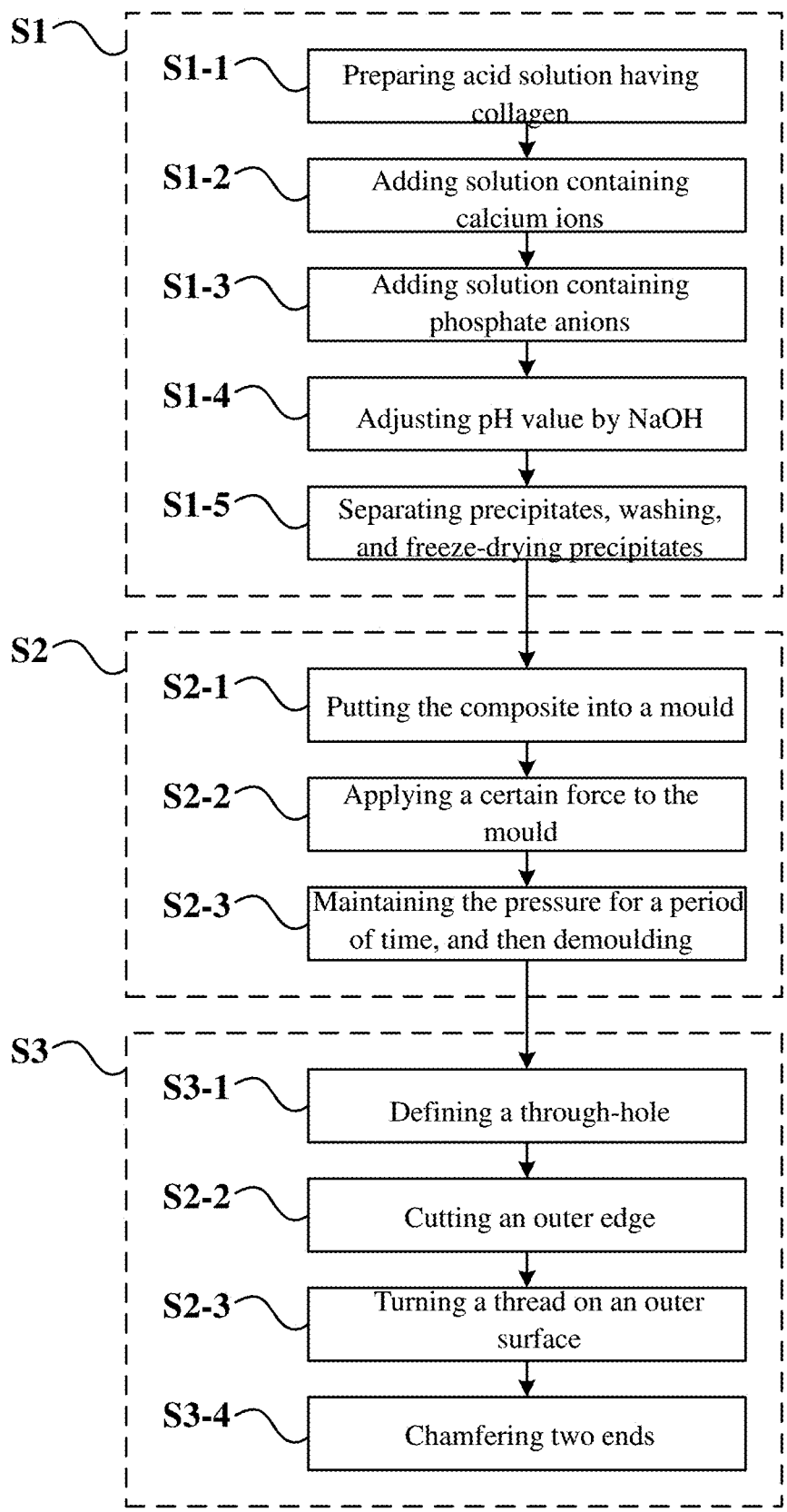
FIG. 1 is a process flow diagram for preparing a mineralized collagen-based femoral head support device according to an embodiment of the present application.

FIG. 1 is a process flow diagram for preparing a mineralized collagen-based femoral head support device according to an embodiment of the present application. According to the steps shown in FIG. 1, the preparation processes of the mineralized collagen-based femoral head support device include:

Step S1-1, 5 g of collagen is dissolved in 10 L of acetic acid solution having a concentration of 0.5 mol/L, and acid solution having collagen is prepared as a result.

Step S1-2, the solution prepared by Step S1-1 is continuously stirred, and 1 L of $CaCl_2$ solution having a concentration of 1mol/L is slowly and dropwise added into the solution prepared by Step S1-1.

Step S1-3, the solution prepared by Step S1-2 is continuously stirred, and 1 L of $Na_2HPO_4$ solution having a concentration of 0.6 mol/L is slowly and dropwise added into the solution prepared by Step S1-2.

Step S1-4, the solution prepared by Step S1-3 is continuously stirred, and NaOH solution having a concentration of 1 mol/L is slowly and dropwise added into the solution prepared in Step S1-3 until the mixed system has a pH of 7.

Step S1-5, after 48 hours standing, the mixed system prepared by Step S1-4 is precipitated; the precipitates are filtered out, washed 5 times with deionized water, and then freeze-dried, and finally grinded; in this way, dry powder is obtained for reserve.

Step S2-1, 6 g of the dry powder obtained by Step S1-5 is weighted and is put into a recess of a mould having a diameter of 11 mm.

Step S2-2, a force is applied to the mould, and the force applied thereto is 100 kN, and then the pressure is relieved; an initial bar formed in the mould is taken out, turned upside down, and further put into the mould again; after that, a force of 100 kN is applied to the mould is again.

Step S2-3, the pressure is maintained for 90 seconds, and then the mould is demoulded in such a way that a mineralized collagen bar is obtained.

Step S3-1, the mineralized collagen bar obtained by Step S2-3 is clamped in a three jaw chuck of a lathe, and a drill having a diameter of 4.0 mm is used to drill the bar from one end along a central axis of the bar; after the drill is drilled into the bar for about half of the length thereof, the bar is taken down, and is reversely clamped at the three jaw chuck; after that, the bar is drilled from the other end thereof, until a through-hole is formed.

Step S3-2, the mineralized collagen bar having a through-hole formed by Step S3-1 is taken down; the bar is sleeved on a frock having a diameter of 4.0 mm, and is further clamped in the three jaw chuck of the lathe, and an outer edge of the bar is cut, until the mineralized collagen bar has an outer diameter of 10 mm.

Step S3-3, thread is turned on an outer surface of the mineralized collagen bar, wherein the thread has a width of 0.5 mm, a depth of 0.5 mm, and a thread pitch of 2.0 mm.

Step S3-4, the mineralized collagen bar is taken down, and two ends thereof are chamfered at an angle of 45 degrees; in this way, a mineralized collagen-based femoral head support device is prepared as a result.

Figure 2:
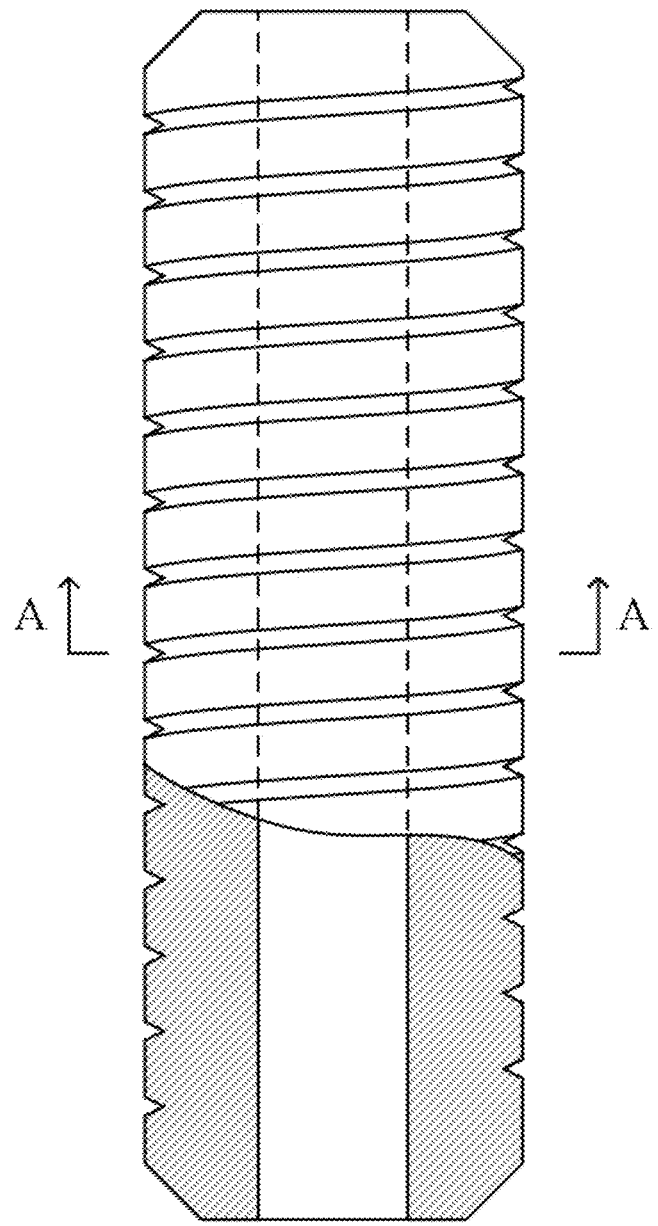
FIG. 2 is a front view of the mineralized collagen-based femoral head support device according to the embodiment of the present application.
Figure 3:
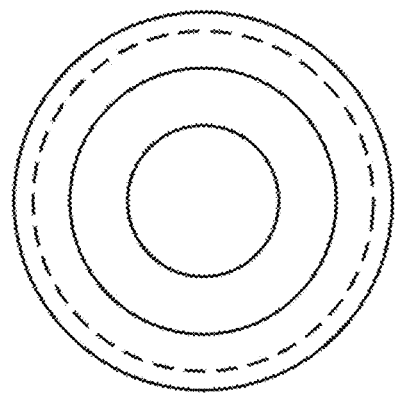
FIG. 3 is a top view of the mineralized collagen-based femoral head support device according to the embodiment of the present application.
Figure 4:
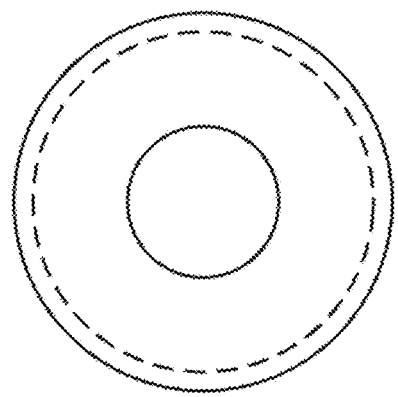
FIG. 4 is a cutaway view of the mineralized collagen-based femoral head support device according to the embodiment of the present application along line A-A.

FIG. 2 is a front view of the mineralized collagen-based femoral head support device according to the embodiment of the present application; FIG. 3 is a top view of the mineralized collagen-based femoral head support device according to the embodiment of the present application; and FIG. 4 is a cutaway view of the mineralized collagen-based femoral head support device according to the embodiment of the present application along line A-A. In this case, the mineralized collagen-based femoral head support device is a cylinder having an upright through-hole, and has an outer diameter of 10.0 mm, a through-hole diameter of 4.0 mm, and a length of 32.0 mm. A thread is formed on the outer surface of the mineralized collagen-based femoral head support device, and the thread has a width of 0.5 mm, a depth of 0.5 mm and a thread width of 2.0 mm.

Figure 5:
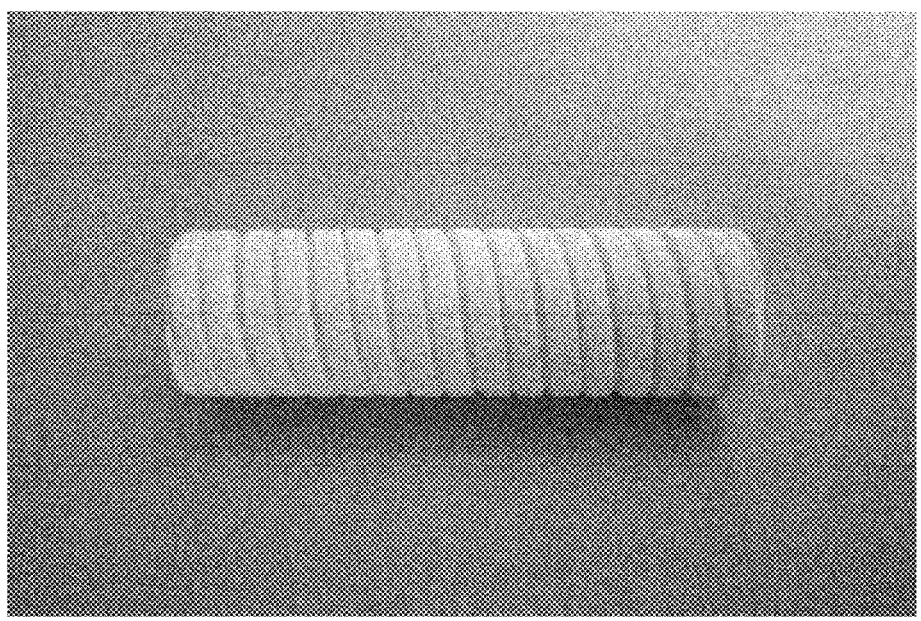
FIG. 5 is a stress-strain curve showing a compressive strength of the mineralized collagen-based femoral head support device according to the embodiment of the present application.

FIG. 5 is a photo of the mineralized collagen-based femoral head support device according to the embodiment of the present application.

Figure 6:
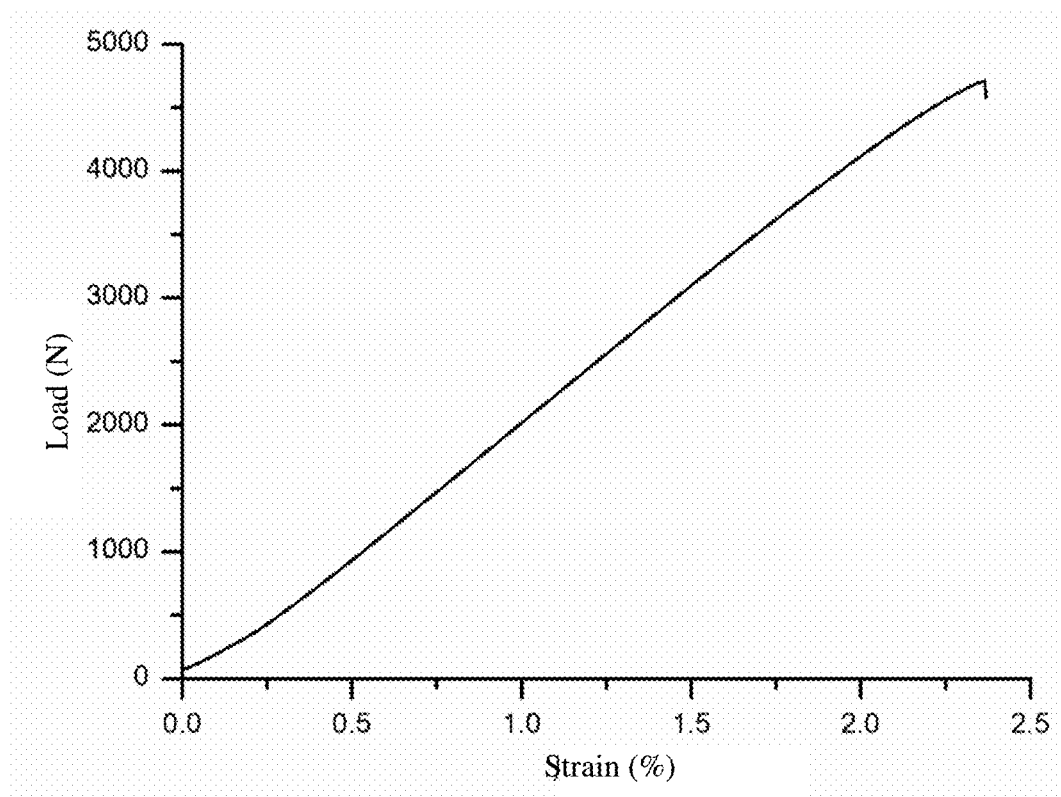
FIG. 6 is a photo of the mineralized collagen-based femoral head support device according to the embodiment of the present application.

FIG. 6 is a stress-strain curve showing a compressive strength of the mineralized collagen-based femoral head support device according to the embodiment of the present application. It can be seen from the graph that, the maximum load in an axial direction of the mineralized collagen-based femoral head support device is 4700N.

The present application is described according to specific embodiments.

However, it can be understood that, one skilled in the art may make various changes and equivalents, without going beyond the protection scope of the present application. In addition, in order to adapt to specific occasions or material, various modification may be made to the present application, without going beyond the protection scope of the present application. Therefore, the present application is not limited to the specific embodiments disclosed herein, and includes all the embodiments which fall into the protection scope of the claims.

The invention claimed is:

1. A preparation method for a mineralized collagen-based femoral head support device, the support device being made from an uniform organic/inorganic composite; the organic phase including collagen; the inorganic phase including nano calcium phosphate salt and a mass ratio of the organic phase to the inorganic phase being 9/1~4/6; the support device having a compressive strength of 4000~6000N in an axial direction thereof; the method comprising the following steps:

Step S1, preparing mineralized collagen powder; wherein the preparation processes include:

Step S1-1, dissolving collagen into hydrochloric acid, nitric acid or acetic acid solution, thereby preparing acid solution having collagen, wherein a concentration of the collagen is $5.0\times10^{-5}$~$5.0\times10^{-3}$ g/mL;

Step S1-2, continuously stirring the solution prepared by Step S1-1, and slowly and dropwise adding solution containing calcium ions; wherein the addition amount of the calcium ions is 0.01~0.16 mol per gram of collagen;

Step S1-3, continuously stirring the solution prepared by Step S1-2, and slowly and dropwise adding solution containing phosphate anions; wherein a molar ratio of the addition amount of the phosphate anions to the addition amount of the calcium ions in Step S1-2 is Ca/P=1/1~2/1;

Step S1-4, continuously stirring the solution prepared by Step S1-3, and slowly and dropwise adding NaOH solution until the mixed system has a pH of 6~8; wherein, when pH=5~6, the mixed system begins to precipitate; when pH=7, white suspension liquid appears in the mixed system;

Step S1-5, after 24~120 hours standing, separating precipitates in the mixed system prepared by Step S1-4, and washing away impurity ions; freeze-drying and grinding the precipitates, thereby obtaining the mineralized collagen powder for reserve;

Step S2, compression moulding a mineralized collagen bar; wherein the moulding processes include:

Step S2-1, weighting a certain amount of the mineralized collagen powder obtained by Step S1-5, and putting the powder into a cylindrical mould having a diameter of 9.0~11.0 mm;

Step S2-2, applying a pressure to the mould, and the pressure applied to the mineralized collagen powder is 900~1200 MPa, and then relieving the pressure; taking out an initial bar formed in the mould, turning the initial bar upside down, and further putting the initial bar into the mould again; applying a pressure to the mould again, and the pressure applied to the mineralized collagen initial bar is 900~1200 MPa;

Step S2-3, maintaining the pressure for 30~300 seconds, demoulding and thereby obtaining the mineralized collagen bar;

Step S3, machining the mineralized collagen bar; wherein the machining processes include:

Step S3-1, clamping the mineralized collagen bar obtained by Step S2-3 in a three jaw chuck of a lathe, drilling the bar from one end of the bar along a central axis thereof by means of a drill having a diameter of 4.0~5.0 mm; after the drill is drilled into the bar for half of the length of the bar, taking down the bar, and reversely clamping the bar at the three jaw chuck; drilling the bar from the other end of the bar until a through-hole is formed;

Step S3-2, taking down the mineralized collagen bar having a through-hole formed by Step S3-1; sleeving the bar on a frock having a diameter of 4.0~5.0 mm; clamping the bar in the three jaw chuck of the lathe, and cutting an outer edge of the bar, until the bar has a required outer diameter;

Step S3-3, turning a thread on an outer surface of the mineralized collagen bar; wherein the thread has a width of 0.25~1.0 mm, a depth of 0.2~0.8 mm, and a thread pitch of 1.5~2.5 mm;

Step S3-4, taking down the mineralized collagen bar, chamfering two ends of the bar at an angle of 45 degrees, thereby obtaining the mineralized collagen-based femoral head support device.

2. The preparation method for a mineralized collagen-based femoral head support device according to claim 1, wherein in the Step S1-1, 5 g of collagen is dissolved in 10 L of acetic acid solution having a concentration of 0.5 mol/L, thereby preparing acid solution having collagen;

in the Step S1-2, the solution prepared by Step S1-1 is continuously stirred, and 1 L of $CaCl_2$ solution having a concentration of 1 mol/L is slowly and dropwise added into the solution prepared by Step S1-1;

in the Step S1-3, the solution prepared by Step S1-2 is continuously stirred, and 1 L of $Na_2HPO_4$ solution having a concentration of 0.6 mol/L is slowly and dropwise added into the solution prepared by Step S1-2; and in the Step S1-4, the solution prepared by Step S1-3 is continuously stirred, and NaOH solution having a concentration of 1 mol/L is slowly and dropwise added into the solution prepared in Step S1-3 until the mixed system has a pH of 7.

3. A mineralized collagen-based femoral head support device prepared by the preparation method according to claim 1, wherein the support device is made from an uniform organic/inorganic composite; wherein the organic phase includes collagen;

the inorganic phase includes nano calcium phosphate salt; and a mass ratio of the organic phase to the inorganic phase is 9/1~4/6;

wherein a length of the nano calcium phosphate salt is 20~200 nm; a molar ratio of the calcium to the phosphate is 1/1~2/1; the device has a compressive strength of 4000~6000 N in an axial direction thereof.

4. The mineralized collagen-based femoral head support device according to claim 3, wherein the device is a cylinder having an upright through-hole, and has an outer diameter of 9.0~11.0 mm, a through-hole diameter of 4.0~5.0 mm, and a length of 30.0~38.0 mm.

5. The mineralized collagen-based femoral head support device according to claim 3, wherein an outer surface of the device has a roughness Ra of 3.2~25.0 μm.

6. The mineralized collagen-based femoral head support device according to claim 3, wherein a thread is formed on an outer surface of the mineralized collagen-based femoral head support device; wherein the thread has a width of 0.25~1.0 mm, a depth of 0.2~0.8 mm, and a thread pitch of 1.5~2.5 mm.

* * * * *